(12) United States Patent
Chmielewski et al.

(10) Patent No.: US 6,459,014 B1
(45) Date of Patent: Oct. 1, 2002

(54) ABSORBENT ARTICLE WHICH MAINTAINS PROLONGED NATURAL SKIN PH

(75) Inventors: Harry J. Chmielewski, Brunswick; Carol L. Erdman, Duluth, both of GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/685,609

(22) Filed: Oct. 11, 2000

Related U.S. Application Data

(60) Provisional application No. 60/165,648, filed on Nov. 15, 1999.

(51) Int. Cl.[7] .............................................. A61F 13/15
(52) U.S. Cl. ....................................... 604/360; 604/375
(58) Field of Search ................................ 604/360, 358, 604/359, 374, 375, 378, 367

(56) References Cited

U.S. PATENT DOCUMENTS 5,334,176 A    8/1994  Buenger et al.
5,716,703 A    2/1998  Payne
5,749,863 A    5/1998  Payne

FOREIGN PATENT DOCUMENTS

WO     WO 94/25077     * 11/1994

* cited by examiner

*Primary Examiner*—Aaron J. Lewis
*Assistant Examiner*—Jamisue Webb
(74) *Attorney, Agent, or Firm*—Christopher C. Campbell; Patrick A. Doody; Hunton & Williams

(57) ABSTRACT

An absorbent article is provided which includes a pH control agent in an amount sufficient to maintain prolonged natural skin pH. The pH control agent can be applied in conjunction with a surfactant. Generally, the pH control agent and optional surfactant can be added to the topsheet, absorbent core, and/or any tissue layer included in the absorbent article. Particularly preferred pH control agents include citric acid and sodium citrate.

5 Claims, 1 Drawing Sheet

ABSORBENT ARTICLE WHICH MAINTAINS PROLONGED NATURAL SKIN PH

RELATED APPLICATIONS

This application claims priority to U.S. Provisional Patent Application Serial No. 60/165,648, filed Nov. 15, 1999, which is incorporated herein by reference.

FIELD OF THE INVENTION

The present invention pertains to an absorbent article, such as a disposable diaper, sanitary napkin, adult incontinence garment, training pant or the like, which includes a pH control agent to help maintain prolonged natural skin pH.

BACKGROUND OF THE INVENTION

Commonly, an absorbent article, such as a disposable diaper, adult incontinent garment, training pant or sanitary napkin, comprises a topsheet which is at least partially liquid permeable, a liquid-impermeable backsheet, and an absorbent core formed from (1) cellulosic fibers, which typically are comminuted softwood pulp fibers, and (2) distributed particles of a superabsorbent polymer (SAP). The absorbent core is generally positioned between the topsheet and the backsheet. It is known to provide the absorbent article with one or more other layers formed from cellulosic fibers or other materials to perform various liquid-absorbing, liquid-distributing, and cushioning functions.

A persistent problem associated with the use of such an absorbent article is "diaper rash", a common form of irritation and inflammation of those parts of user's body normally in contact with the, absorbent article. It is generally accepted that true "diaper rash" or "diaper dermatitis" is a condition which is, in its most simple stages, a contact irritant dermatitis. The irritation of simple diaper rash results from extended contact of the skin with urine, or feces, or both. The most commonly accepted list of factors linked to diaper rash includes ammonia, bacteria, the products of bacterial action, urine pH, Candida albicans, and moisture.

More specifically, a primary cause of diaper rash is believed to be a particular set of conditions which arises as a result of prolonged contact of skin with mixtures of feces and urine. Activity of proteolytic and lipolytic fecal enzymes present in such a mixture is believed to be a major factor in producing skin irritation. Further, urease excreting bacteria facilitate the degradation of urea into ammonia, thereby increasing the pH of urine and fecal matter which in turn raises skin pH. This rise in skin pH, for example to levels of 6.0 and above, increases the fecal proteolytic and lipolytic enzymatic activity which may produce diaper rash. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation. However, when skin pH is kept at natural levels, i.e., between about 4.5 and about 6.0, the skin's barrier properties can be maintained.

The foregoing diaper rash model suggests that effective diaper rash control can be achieved by maintaining natural skin pH to thereby inhibit irritation-producing enzymatic activity while simultaneously maintaining the absorbent article environment as dry as possible.

Absorbent articles, compositions and procedures which incorporate buffers and/or acidifying agents into absorbents articles for controlling skin pH are known. For example, see U.S. Pat. No. 4,685,909 to Berg et al. ("Berg"). Berg discloses absorbent articles having acidic pH control agents and absorptive hydrogel materials non-uniformly distributed in distinct, discrete zones within the absorbent article. Berg teaches that the simple combination of pH control agents and absorptive hydrogel materials is not desirable, and that instead the components should be separated into discrete zones. By separating hydrogel materials and pH control agents in this manner, Berg concludes that skin pH can be controlled in the presence of urine and fecal matter to combat diaper rash without adversely affecting the ability of the hydrogel to absorb fluids and maintain skin dryness. Further, Berg teaches that the pH control agents should be present at relatively high levels ranging from about 1% to 30% by weight, based on the total weight of the absorbent article. Therefore, the absorbent article taught by Berg is disadvantageous in that it requires the presence of relatively large amounts of pH control agents. Further, the manufacturing processes are complicated by the necessary steps involved in separating the pH control agent from the absorbent material in the core.

Another approach in the prior art for combating diaper rash is the incorporation of a pH control agent into a lotion which is then deposited on the topsheet of an absorbent article. For instance, U.S. Pat. No. 5,525,346 to Hartung et al. discloses a diaper wherein at least a portion of the diaper that will contact the user's skin is impregnated with a lotion that includes a pH control agent. Further, the pH control agent is preferably included in the lotion in an amount of at least 3.5% by weight, based on the total weight of the lotion. Again, such a lotioned diaper is cumbersome in that the manufacturing process is complicated by the inclusion of additional steps necessary for applying the lotion to the diaper. Further, such a lotioned diaper is economically burdensome due to the increased costs associated with the additional processing steps, and the lotion itself.

Therefore, among other things, this invention has resulted from ongoing efforts to produce an absorbent article which is capable of maintaining natural skin pH in an effective, prolonged, and economical manner.

SUMMARY OF THE INVENTION

Accordingly, an object of the present invention is to provide an absorbent article which comprises a pH control agent to maintain prolonged natural skin pH.

Another object of the present invention is to provide an absorbent article comprising a topsheet, wherein at least a portion of the topsheet includes a pH control agent, such as citric acid or sodium citrate, in an amount sufficient to maintain prolonged natural skin pH.

The invention further relates to an absorbent article comprising a topsheet and an absorbent core wherein at least a portion of the topsheet and at least a portion of the absorbent core include a pH control agent in an amount sufficient to maintain prolonged natural skin pH.

These and other objects, features and advantages of this invention are evident from the following description of a preferred embodiments of this invention, with reference to the accompanying drawings.

DETAILED DESCRIPTION OF THE PREFERRED EMBODIMENTS

Figure 1:
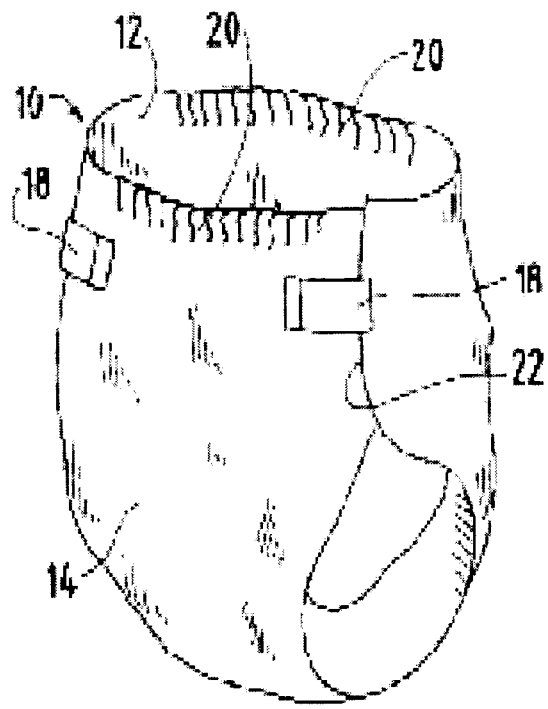
FIG. 1 is a fragmentary, perspective view of a disposable diaper exemplifying an absorbent article according to this invention, in an assembled condition.

The present invention is directed to an absorbent article such as a diaper, training pant, adult incontinent product, sanitary napkin, or the like, which includes a pH control agent in an amount sufficient to maintain prolonged natural skin pH.

The term "natural skin pH" means a skin pH between about 4.5 and 6. Skin pH is determined by placing the flat tip of a pH electrode against the skin. The electrode is then held in place for at least 60 seconds using firm pressure to guarantee good contact with the skin. The pH measurement is then taken after 60 seconds, or upon the electrode reaching equilibrium, which ever occurs first.

The term "maintain prolonged natural skin pH" means that natural skin pH is maintained for an extended period of time, both while the user's skin is in direct contact with moisture, urine, and/or feces within the absorbent article environment, and after the user's skin has been allowed to dry and/or is no longer in contact with the absorbent article.

As stated above, the absorbent article of the present invention includes a pH control agent in an amount sufficient to maintain prolonged natural skin pH. A wide variety of non-toxic, non-irritating acidic materials which release protons can serve as pH control agents. For instance, these materials can be low molecular weight organic or inorganic acids, high molecular weight polymeric acids or ion exchange resins and fibers in the hydrogen form. Particularly preferred pH control agents include citric acid and sodium citrate.

While not wishing to be bound by theory, it is believed that the pH control agent works by two mechanisms: (1) by lowering the pH of any moisture, urine, and/or feces that come into direct contact with the skin of the user; and (2) by depositing the active ingredient of the pH control agent onto the skin of the user to enhance and prolong the natural buffering capacity of the skin. The deposition of the active ingredient of the pH control agent onto the skin of the user can occur both through dry and/or wet transfer within the absorbent article environment.

The absorbent article of the present invention can include the pH control agent in at least a portion of any of its interior component parts in an amount sufficient to maintain prolonged natural skin pH. For instance, the pH control agent can be included in at least a portion of the topsheet, the absorbent core, and/or any tissue, distribution, or transfer layer. It is particularly preferred that a component part of the absorbent article which comes into substantial contact with the skin of the intended user, e.g., the topsheet, includes the pH control agent. In another preferred embodiment, the pH control agent can be included in at least a portion of; the absorbent core and at least a portion of the topsheet or tissue layer. although any single component part or combination of component parts is within the scope of the present invention.

Preferably, when the component part that includes the pH control agent is the topsheet or any tissue, distribution, or transfer layer, the pH control agent is included in the treated portion of the component part in an amount sufficient to result in a dry add-on of at least about 1% by weight, preferably from about 1% by weight to about 10% by weight, and more preferably about 2% by weight of the pH control agent, based on the total weight of the treated portion of the component part. In a particularly preferred embodiment, the treated portion of the topsheet of the absorbent includes a dry add-on amount of about 2% by weight citric acid, based on the total weight of the treated portion of the topsheet. In other terms, in a particularly preferred embodiment, the treated portion of the topsheet includes 0.02 g/m$^2$ of citric acid, based on a 16 gsm topsheet. By way of example, a standard large diaper having such a topsheet (40.3 g total weight) would include only about 0.05% by weight citric acid, based on the total weight of the diaper.

When the component part that includes the pH control agent is the absorbent core of the absorbent article, the absorbent core preferably includes the pH control agent in a dry add-on amount of up to about 1% by weight, more preferably about 0.9% by weight, based on the total weight of the treated portion of the absorbent core.

The pH control agent can be applied to the treated portion of the component part of the absorbent, article by any method known in the art, including kiss-coating and spraying methods. Suitable kiss-coating and spraying methods are disclosed in U.S. Pat. No. 5,620,788 to Garavaglia et al. and U.S. Pat. No. 5,635,191, the disclosures of which is incorporated herein by reference in a manner consistent with this disclosure. However, it should be understood that the practice of the present invention is not limited to the above-described methods.

Preferably, the pH control agent is applied to the treated portion of the component part of the absorbent article as an aqueous solution comprising the pH control agent. The aqueous solution can be prepared, for example, by dissolving the pH control agent in water at a dilution ratio ranging from about 200 to about 2000, depending on the method of application of the pH control agent to the treated portion of the component part. This method of preparation is applicable to spray and kiss-coat (also known as etched roll or gravure roll) applications.

The target dry add-on concentration can be achieved by adjusting the concentration of the total solids in the aqueous solution and the amount of aqueous solution applied to the treated portion of the component part of the absorbent article. Those skilled in the art will recognize many ways to arrive at the preferred target dry concentration by appropriate modification of the foregoing preferred levels for specific methods of application.

After the treated portion of the component part of the absorbent article is wetted with the aqueous solution, it is preferably dried by, e.g., directing the component part through a forced hot air oven or across a bank of infrared lights, steam cans, dielectric dryers or other conventional driving apparatuses as are known to those skilled in the art. The component part of the absorbent article typically moves across the heating medium at the same line speed at which the aqueous solution is applied. Typical line speeds for application of the aqueous solution are around 500–1000 ft/min.

In a preferred embodiment, the pH control agent can be applied to the treated portion of the component part of the absorbent article in conjunction with a surfactant. While not wishing to be bound by theory, it is believed that the surfactant facilitates the application of the pH control agent to the surface of the treated portion of the component part by lowering the surface tension of the solution containing the pH control agent.

The surfactant can be any known surfactant suitable for use in hygienic applications, as is generally known in the art, and should lower the surface tension of water to a value less than the apparent surface free energy of the component part. For example, an untreated polypropylene nonwoven fabric typically has an apparent surface free energy of about 36 dynes/cm$^2$. Polyester nonwoven, used as a transfer layer, has a surface free energy of about 43 dynes/cm$^2$ Particularly preferred surfactants for use in the present invention include, but are not limited to, TRITON™ GR-5M and SILASTOL™ PST.

The surfactant can be present in an aqueous solution comprising the pH control agent at an amount sufficient to lower the surface tension of the aqueous solution to a level below about 40 dynes/cm$^2$, more preferably below about 35 dynes/cm$^2$, and most preferably below about 32 dynes/cm$^2$. At these surface tensions, the pH control agent can effectively wet the treated portion of the component part of the absorbent article. Generally, a surfactant is preferably employed in an amount sufficient to result in a dry add-on weight of between about 0.05% and 0.8% by weight, based on the total weight of the treated portion of the component part.

By way of example, but without intending to limit the invention, dioctyl sodium sulfosuccinate sold as TRITON™ GR-5M (manufactured by Union Carbide of Danbury, Conn.) is typically applied to spunbonded nonwoven so that, when dry, it comprises from about 0.05% to about 0.8% by weight, based on the total weight of the non-woven. Alternatively, SYNTHESYN™ FPC may be applied to the nonwoven. Another surfactant, SILASTOL™ PST (manufactured by Schill & Seilacher of Böblingen, Germany), is recommended to be applied at a rate so that, when dry, it comprises about 0.05% to about 0.8% by weight, based on the total weight of the non-woven.

In a particularly preferred embodiment of the present invention, the absorbent article is a diaper which comprises a topsheet, a backsheet, and an absorbent core. The pH control agent is selected from the group consisting of citric acid and sodium citrate, and is applied to the topsheet of the diaper in conjunction with a surfactant. Further, the topsheet preferably includes the pH control agent at a dry add-on amount of between about 1% and 10% by weight, based on the total weight of the treated portion of the topsheet, and includes the surfactant at a dry add-on amount of between about 0.05% and about 0.8% by weight, based on the total weight of the treated portion of the topsheet.

Figure 2:
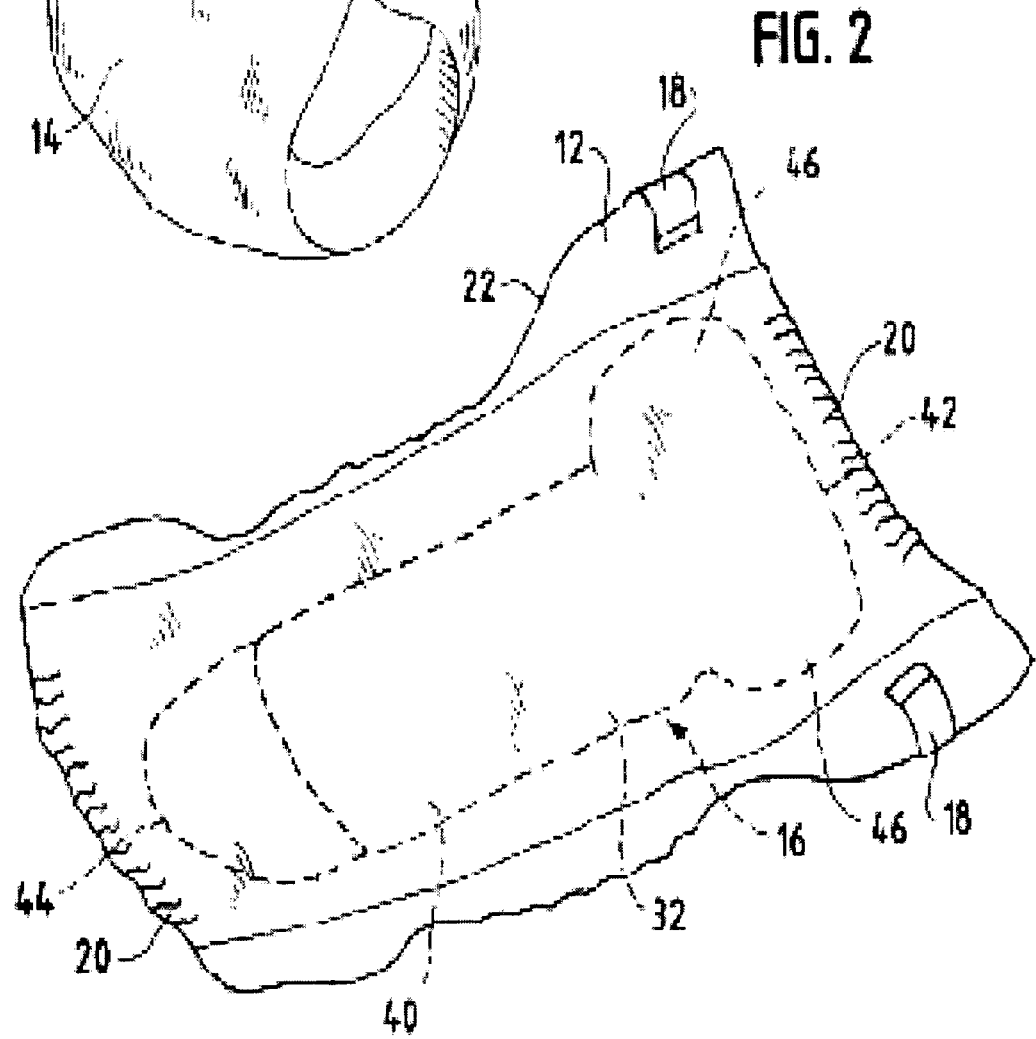
FIG. 2 is a fragmentary, perspective view of the disposable diaper of FIG. 1, in a flattened condition.

As shown in FIGS. 1 and 2, the component part treated with the pH control agent may be employed, for example in a disposable diaper 10. The disposable diaper 10 may be appropriately sized for infant use or for adult use. If sized for adult use, the disposable diaper 10 may be also called an incontinent garment. It may be here noted that this invention may be also embodied in a wound dressing or another absorbent article other than a disposable diaper, e.g., training pant, adult incontinence garment, sanitary napkin, or the like.

Broadly, the disposable diaper 10 comprises a topsheet 12 as described above, a liquid-impermeable backsheet 14, and an absorbent structure 16 positioned between the topsheet 12 and the backsheet 14. The disposable diaper 10 has tape fasteners 18, elasticized waistbands 20, and other features well known to those skilled in the art. The topsheet 12 and the backsheet 14 may be bonded adhesively around outer edges 22 of the disposable diaper 10, in a known manner, so as to encapsulate the absorbent structure 16. The topsheet 12, also called a facing sheet, may be made from polymeric fibers such as polyolefins. The backsheet 14 may be made from a synthetic polymeric film, such as a polyethylene film.

Except as illustrated and described herein, the disposable diaper 10 may be substantially similar to the disposable diaper disclosed in Huffman et al. U.S. Pat. No. 5,403,301, or in Chmielewski U.S. Pat. No. 5,891,120, both assigned to the assignee of the present invention. the disclosures of which are incorporated herein by reference in a manner consistent with this disclosure. As shown in FIG. 2, the absorbent core 32 has an elongate, central portion 40 with a front end 42 and a back end 44, along with two ears 46 near the front end.

Except as illustrated and described herein, the disposable diaper 10 may be substantially similar to the disposable diaper disclosed in Huffman et al. U.S. Pat. No. 5,403,301, or in Chmielewski U.S. Pat No. 5,891,120, both assigned to the assignee of the present invention, the disclosures of which are incorporated herein by reference in a manner consistent with this disclosure. As shown in FIG. 2, the absorbent core 32 has an elongate, central portion 40 with a front end 42 and a back end 44, along with two ears 46 near the front end 42. The disposable diaper 10 may also include at least one tissue layer 45 between the topsheet 12 and the backsheet 14. In a preferred embodiment, the absorbent structure 16 includes an upper layer near the topsheet 12, a lower layer near backsheet 14, and an absorbent core positioned between the upper layer and the lower layer. The upper layer and lower layer may be tissue layers 45.

In a particularly preferred embodiment, at least a portion of the topsheet 12 includes the pH control agent according to the present invention to maintain prolonged natural skin pH. In one embodiment, at least 50% of the surface of the topsheet includes the pH control agent. Preferably, the portion of the topsheet 12 including the pH control agent is that portion which generally corresponds in location to the absorbent core 32, and more preferably that portion which corresponds in location to the central portion 40 of the absorbent core 32.

The following examples are designed to illustrate particular embodiments of the present invention and demonstrate the efficacy of the present invention as compared to conventional surfactant containing absorbent articles.

EXAMPLE 1

Preparation of Topsheet with 2% Dry Add-On of pH Control Agent

This example describes the production of top sheet useful in an absorbent article of the present invention. The topsheet so produced includes a pH control agent and a surfactant in an amount sufficient to maintain prolonged natural skin pH.

An aqueous solution comprising the pH control agent and the surfactant was initially produced, and the aqueous solution was then applied to the topsheet material. In particular, the aqueous solution was prepared by first dissolving the surfactant in approximately 50 ml to 75 ml of deionized water, and then adding the pH control agent and additional deionized water to the surfactant solution. The resulting pH control agent/surfactant aqueous solution was then stirred for approximately 5 minutes. The topsheet material was submerged in the pH control agent/surfactant aqueous solution and stirred until completely saturated with the aqueous solution. Excess solution was removed from the topsheet and the samples were air dried. The materials and amounts used are detailed below in Table 1. The topsheet used was a 15 gsm spunbond nonwoven. The "Amount*" listed in Table 1 refers to the weight percent of the indicated component in the total pH control agent/surfactant aqueous solution. The balance of the aqueous solution is deionized water. The citrate buffer consisted of 75% by weight sodium citrate and 25% by weight citric acid, based on the total weight of the citrate buffer.

TABLE 1

| Surfactant | | pH Control Agent | | Add-On (mg) | | Add-On (%) | |
|---|---|---|---|---|---|---|---|
| Type | Amount* | Type | Amount* | Surf. | pH Agent | Surf. | pH Agent |
| GR5M | 0.19% | Citric Acid | 1.25% | 3.4 mg | 23.0 mg | 0.29% | 1.92% |
| GR5M | 0.19% | Citric Acid | 1.25% | 4.1 mg | 27.5 mg | 0.35% | 2.33% |
| GR5M | 0.19% | Citric Acid | 1.25% | 3.8 mg | 25.5 mg | 0.31% | 2.09% |
| GR5M | 0.19% | Citrate Buf. | 1.25% | 3.9 mg | 25.7 mg | 0.31% | 2.09% |
| GR5M | 0.19% | Citrate Buf. | 1.25% | 3.5 mg | 23.1 mg | 0.28% | 1.85% |
| GR5M | 0.19% | Citrate Buf. | 1.25% | 3.6 mg | 24.0 mg | 0.29% | 1.92% |

EXAMPLE 2

Buffering Ability of Topsheet Including 2% pH Control Agent

This Example demonstrates the pH buffering ability of topsheet materials prepared according to the present invention. Test squares of standard nonwoven were prepared in accordance with Example 1 to include standard surfactant and approximately 2% by weight of citric acid. The samples were placed into small weigh boats and dosed with 0.2 ml of 0.1% ammonium hydroxide saline solution with a pH of 9.76. After 10 minutes, the pH of the samples we re measured at equilibrium, as indicated in Table 2. Control samples including only standard surfactant were also tested.

TABLE 2

| Sample | pH1 | pH2 | pH3 | pH4 | pH5 | AVG. pH |
|---|---|---|---|---|---|---|
| 2% Citric Acid | 6.28 | 5.32 | 5.48 | 5.60 | 5.00 | 5.54 |
| Control | 8.76 | 8.72 | 8.50 | 8.08 | 8.16 | 8.44 |

EXAMPLE 3

Skin pH Buffering Ability of Topsheet with 2% pH Control Agent

This Example demonstrates the ability of a topsheet material of the present invention to maintain prolonged natural skin pH, both while the skin is in contact with high pH liquid and after the skin is allowed to dry. The nonwoven topsheet test samples were prepared according to Example 1. Initially, the natural skin pH of the test subject was measured at two test site locations. A 20 mm×20 mm of nonwoven topsheet sample was then placed on the test sites. One topsheet sample was a control sample including only standard surfactant. One topsheet sample was a test sample including 2% by weight of citric acid and standard surfactant. Once the topsheet samples were in place, 0.1 ml of 0.1% ammonium hydroxide saline solution were dosed on the topsheet samples. The dosed topsheet samples were then covered with poly and secured with tape around the edges. After 15 minutes, the poly and the tape were removed, and the pH of the wet topsheet samples on the skin were measured. The topsheet samples were then removed, and the skin was allowed to air dry. The pH of the dry skin at the test sites were then measured. All pH readings were taken at 60 seconds from the time the pH electrode was placed on the test site. The results are indicated below in Table 3.

TABLE 3

| | Initial Dry Skin pH | | Treated Skin pH | | Dry Skin pH | |
|---|---|---|---|---|---|---|
| | | | Site 1 Control- | Site 2 2% Citric | Site 1 Control- | Site 2 2% Citric |
| Sample | Site 1 | Site 2 | treated | Acid-treated | treated | Acid-treated |
| 1 | 5.37 | 5.16 | 7.92 | 6.92 | 6.41 | 5.53 |
| 2 | 4.90 | 5.56 | 7.52 | 6.00 | 6.82 | 6.11 |
| 3 | 5.68 | 5.52 | 7.78 | 7.96 | 6.96 | 5.75 |
| 4 | 4.85 | 5.16 | 6.48 | 7.35 | 6.30 | 5.48 |
| 5 | 5.90 | 6.17 | 7.58 | 5.06 | 6.69 | 4.81 |
| 6 | 5.20 | 4.82 | 8.20 | 6.39 | 6.23 | 6.05 |
| 7 | 5.62 | 5.46 | 7.36 | 7.12 | 6.59 | 6.30 |

As Table 3 demonstrates, topsheet samples including 2% citric acid outperformed standard topsheet in their ability to maintain natural skin pH while the skin was in direct contact with high pH liquid. Further, Table 3 demonstrates the unexpected ability of topsheet materials prepared according to the present invention to maintain prolonged natural skin pH even after the skin dries.

EXAMPLE 4

Clinical Study

A particularly preferred embodiment of the present invention was tested in a two week clinical trial. In this Example, a disposable diaper comprising 0.9% by weight citric acid treated pulp in the absorbent core and a nonwoven topsheet including 2% by weight citric acid and 0.3% by weight Triton GR5M surfactant was evaluated in a paired t-test comparing average skin pH over a two week period. The control diaper contained standard pulp and a standard topsheet including with 0.3% by weight Triton GR5M surfactant. The topsheet material was a 15 gsm white spunbond nonwoven material from Polybond. Participants were divided into two test groups, one group used the test diapers during the first week followed by the control diaper during the second week. The other group used the control diaper during the first week followed by the test diaper during the second week. At the conclusion of each of the weeks, the test subjected skin pH was measured. 27 participants completed the study.

Eighty-five percent of the participants wearing the control diaper the first week and the test diaper the second week had a decrease in skin pH from an average of 6.54 to 5.53. This is statistically significant with a 99% confidence. Participants wearing the test diaper the first week and the control diaper the second week showed a directional increase in pH form an average of 5.45 to 5.79. This increase was not statistically significant, however. Only 57% of the participants had an increase in skin pH, and 7% were unchanged. There was not a statistically significant difference in the bulk pH of the diapers. Further, average pH and urine volumes were the same for each group, and there was not a correlation between urine volume and pH.

This study again conclusively demonstrates the ability of absorbent articles of the present invention to maintain natural skin pH. This study also shows the unexpected ability of the present invention to maintain prolonged natural skin pH over an extended period of time, even after the skin is no longer in contact with the absorbent article including the pH control agent. Further, the absorbent article of the present invention can maintain prolonged natural skin pH through repeated high pH insults, even after the skin is no longer in contact with the pH control agent.

As is obvious to one of ordinary skill in the art, various modifications may be made in the preferred embodiments without departing from the scope and spirit of this invention.

What is claimed is:

1. An absorbent article which maintains prolonged natural skin pH comprising:

a) a topsheet which is at least partially liquid pervious;

b) a liquid impervious backsheet joined to said topsheet;

c) an absorbent core positioned between said topsheet and said backsheet; wherein at least a portion of said topsheet and at least a portion of said absorbent core include a pH control agent selected from the group consisting of citric acid and sodium citrate; and wherein the at least a portion of said topsheet includes the pH control agent in a dry add-on amount ranging from about 1% by weight to about 10% by weight, based on the total weight of the at least a portion of said topsheet.

2. The absorbent article of claim 1 wherein said pH control agent is citric acid.

3. The absorbent article of claim 1 wherein said pH control agent is applied to the at least a portion of said topsheet in conjunction with a surfactant.

4. The absorbent article of claim 3 wherein said surfactant is added to the at least a portion of said topsheet in a dry add-on amount ranging from about 0.05% by weight to about 0.8% by weight, based on the total weight of the at least a portion of said topsheet.

5. The absorbent article of claim 1 wherein at least a portion of said absorbent core includes said pH control agent in an amount of up to about 1% by weight, based on the total weight the of at least a portion of said absorbent core.

* * * * *